United States Patent [19]

Tong

[11] Patent Number: 5,171,743

[45] Date of Patent: Dec. 15, 1992

[54] COMPOUNDS COMPOSITION AND USE OF SUBSTITUTED 1,3-DITHIOLO- AND 1,4-DITHINO-PYRIDINES AS AN ANTIMICROBIAL

[75] Inventor: Yulan C. Tong, Walnut Creek, Calif.

[73] Assignee: The Dow Chemical Company, Midland, Mich.

[21] Appl. No.: 811,132

[22] Filed: Dec. 20, 1991

[51] Int. Cl.$^5$ .................... A01N 43/40; C07D 495/04
[52] U.S. Cl. ..................................... 514/301; 546/114
[58] Field of Search ......................... 546/114; 514/301

[56] References Cited

U.S. PATENT DOCUMENTS

| | | | |
|---|---|---|---|
| 2,166,661 | 6/1937 | Hopkins | 546/114 |
| 3,761,475 | 9/1973 | Kurihara et al. | 546/114 |
| 3,829,425 | 8/1974 | Kurihara et al. | 546/114 |
| 3,849,415 | 11/1974 | Kurihara et al. | 546/114 |
| 4,038,393 | 7/1977 | Mixan et al. | 544/350 |
| 4,168,174 | 9/1979 | Mixan | 106/16 |
| 4,172,133 | 10/1979 | Wilson et al. | 544/345 |
| 4,199,581 | 4/1980 | Mixan et al. | 544/345 |
| 4,210,645 | 7/1980 | Wilson et al. | 544/345 |
| 4,625,035 | 11/1986 | Werner | 546/345 |
| 4,835,153 | 5/1989 | Kubota et al. | 544/350 |
| 4,863,925 | 9/1989 | Kubota et al. | 544/350 |

FOREIGN PATENT DOCUMENTS 1-215069  8/1989  Japan.

OTHER PUBLICATIONS

Derwent Publication 89-290597, Ricoh KK, Feb. 24, 1988, JA 1215-069-A.

Primary Examiner—Bernard Dentz

[57] ABSTRACT

Substituted 1,3-dithiolo- and 1,4-dithiino-pyridines are prepared which correspond to the formula:

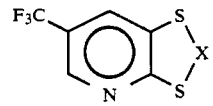

wherein X represents:

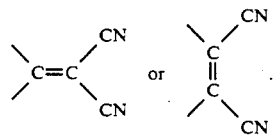

These compounds have been found to exhibit antimicrobial activity in industrial and commercial applications and compositions containing these compounds are so employed.

11 Claims, No Drawings

COMPOUNDS COMPOSITION AND USE OF SUBSTITUTED 1,3-DITHIOLO- AND 1,4-DITHINO-PYRIDINES AS AN ANTIMICROBIAL

BACKGROUND OF THE INVENTION

The field of this invention is novel substituted pyridine compounds and their use as antimicrobial agents.

U.S. Pat. No. 3,761,475 discloses the preparation of compounds of the formula:

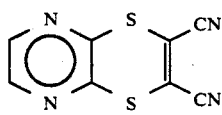 

and

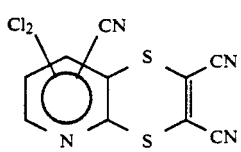 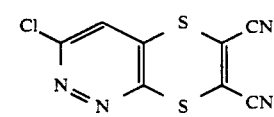

which are useful as fungicides and bactericides.

U.S. Pat. No. 4,168,174 discloses the preparation of compounds of the formula:

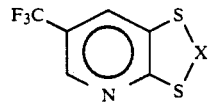

and

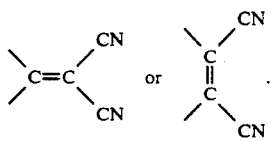

which are useful for preventing marine antifouling.

Japanese Patent 01215-069-A discloses a compound of the formula:

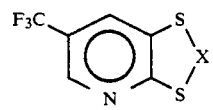

wherein $R_3$ and $R_4$ may be cyano and $R_1$ and $R_2$ may form a substituted heterocyclic aromatic ring. This compound is useful in a photoactive layer in a photoelectric conversion element.

The desirability of identifying or discovering new antimicrobial agents is widely recognized. New antimicrobial agents are desired for several reasons; these include, but are not limited to, responding to the problem created by the development of microbe strains resistant to known antimicrobials, the occurrence of undesirable interactions of certain known antimicrobials with the medium or product in which the antimicrobial is used, and high toxicity of certain known antimicrobials to certain non-target organisms such as mammals.

The present invention solves these problems by disclosing new compounds which may be employed as an antimicrobial.

SUMMARY OF THE INVENTION

The present invention is a compound corresponding to the formula:

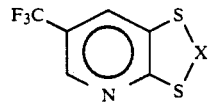

wherein X represents:

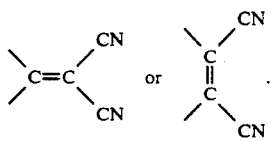

The present invention is also an antimicrobial composition comprising an inert diluent and an antimicrobially effective amount of a compound corresponding to the formula:

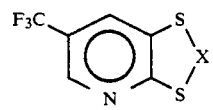

wherein X represents:

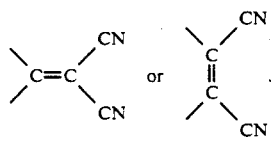

The present invention is also a method for inhibiting microorganisms in a microbial habitat comprising contacting said microbial habitat with an antimicrobially effective amount of a compound corresponding to the formula:

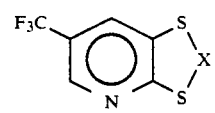

wherein X represents:

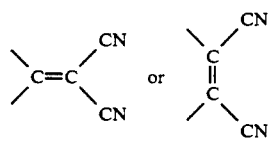

DETAILED DESCRIPTION OF THE INVENTION

The present invention is a compound corresponding to the formula:

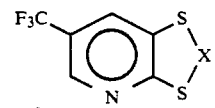

wherein X represents:

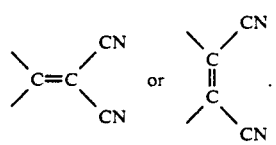

The 6-(trifluoromethyl-1,3-dithiolo-[4,5-b]pyridine-2-yldienyl propanedinitrile compound of the present invention wherein X represents:

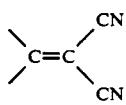

may be prepared, for example, by the reaction of 2,3-difluoro-5-(trifluoromethyl)pyridine with di(sodiomercapto)-methylenemalononitrile or di(potassiomercapto)-methylenemalononitrile. The general reaction scheme for this reaction is as follows:

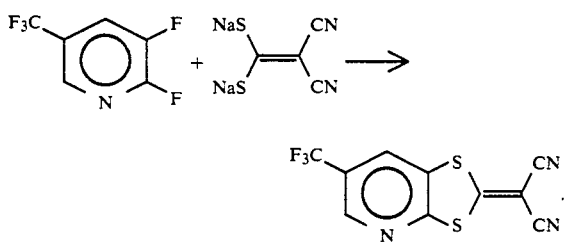

The use of di(sodiomercapto)-methylenemalononitrile to prepare other compounds is known and is generally disclosed in U.S. Pat. Nos. 4,038,393; 4,075,204 and 4,075,205.

The 7-(trifluoromethyl)-dithiino[2,3-b]pyridine-2,3-dicarbonitrile compound of the present invention wherein X represents:

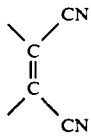

may be prepared by the reaction of 2,3-difluoro-5-(trifluoromethyl)pyridine with disodium dimercaptomaleonitrile. The general reaction scheme for this reaction is as follows:

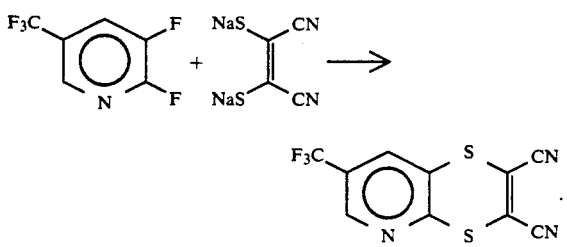

The use of disodium dimercaptomaleonitrile to prepare other compounds is known and is generally disclosed in U.S. Pat. Nos. 3,761,475; 4,172,133; 4,199,581 and 4,210,645.

In carrying out these reactions, the 2,3-difluoro-5-(trifluoromethyl)pyridine and the di(sodiomercapto) or di(potassiomercapto)-methylenemalononitrile and/or disodium dimercaptomaleonitrile are typically contacted together in substantially equimolar amounts in a suitable solvent. Suitable solvents include those such as dimethylformamide or dimethyl sulfoxide. Elevated reaction temperatures, typically from about 30° C. to about 100° C., may be used in order to speed up the reaction.

Preparation of Starting Materials

The synthesis of 2,3-difluoro-5-(trifluoromethyl)pyridine is straightforward and is described in the art, such as in U.S. Pat. No. 4,625,035.

The synthesis of (sodiomercapto)-methylenemalononitrile is straightforward and is described in the art, such as in A. Adams et al., *J. Chem Soc.*, 3061 (1959).

The synthesis of disodium dimercaptomaleonitrile is straightforward and is described in the art, such as in Muetterties, *Inorganic Synthesis*, Volume X, Page 11.

The following examples illustrate the present invention and the manner by which it can be practiced but, as such, should not be construed as limitations upon the overall scope of the same.

EXAMPLE 1

Preparation of 6-(Trifluoromethyl)-1,3-Dithiolo[4,5-b]Pyridine-2-Ylidenyl Propanedinitrile In a reaction flask are mixed 12 grams (0.05 mole) of di(sodiomercapto)-methylenemalononitrile and 9.15 grams (0.05 mole) of 2,3-difluoro-5-(trifluoromethyl)-pyridine in 100 ml of dimethyl sulfoxide. The reaction mixture is heated at 80° C. for 24 hours. After cooling, the reaction mixture is poured into 500 grams of ice-water and extracted with dichloromethane. The organic solution is dried and concentrated to 50 ml and diluted with 25 ml of hexane, and cooled. An orange precipitate is collected and dried. The precipitate is recrystallized from 2-propanol/dichloromethane and ether/dichloromethane to give 2.3 grams (16 percent yield) of product which has a melting point of 163° to 166° C.

The structure identity is confirmed by proton nuclear magnetic resonance spectroscopy ($^1$H), carbon nuclear magnetic resonance spectroscopy (NMR), infrared spectroscopy (IR) and gas chromatography/mass spectrometry (GC/MS).

EXAMPLE 2

Preparation of 6-Trifluoromethyl-1,3-Dithiolo[4,5-b]Pyridine-2-Ylidenyl Propanedinitrile A 500 ml roundbottom flask fitted with mechanical stirring, thermowell, condenser and a nitrogen bleed, is charged with 125 ml of N,N-dimethylformamide (DMF) and 60 g (0.25 moles) of dipotassium dimercaptomethylenemalononitrile. The reaction mixture is stirred and heated to 33° C. and 36.6 g (0.2 moles) of 2,3-difluoro-5-(trifluoromethyl)pyridine is added. The temperature slowly increases to 45° C. and is then maintained at 50° C. for 4½ hours. The reaction is quenched by pouring the solution into 2 liters of 50° C. water. The resulting slurry is allowed to cool slowly to 30° C. with occasional stirring, and is then filtered and washed with water. The recovered dry product weighs 45.5 g (80 percent yield) and has a melting point of 170°–172° C.

EXAMPLE 3

Preparation of 7-(Trifluoromethyl)-Dithiino[2,3-b]Pyridine-2,3-Dicarbonitrile

Disodium dimercaptomaleonitrile, 16.4 grams (89 percent pure, 0.0793 mole), is dissolved in 75 ml of dimethyl formamide and cooled to 15° to 20° C., while 14.5 grams (0.0793 mole) of 2,3-difluoro-5-(trifluoromethyl)pyridine is added in slowly. After addition is complete, the reaction mixture is stirred at 20° C. for 1 hour and then at 90° C. for 24 hours. The reaction mixture is then poured into ice and stirred. The solution is decanted off and a semi-solid residue is dissolved in dichloromethane, washed with water, treated with charcoal and dried. After removal of magnesium sulfate drying agent, the solution is mixed with 75 grams of silica gel and evaporated to dryness. The solid is put on a sintered glass funnel and eluted with 2 percent acetone in hexane. Fractions with mostly a first major component are combined and recrystallized from ether to give 1.5 grams (5.3 percent yield) of an off-white solid. This material is analyzed and found to be bis(3-hydroxy-5-(trifluoromethyl)pyridin-2-yl)sulfide, corresponding to the structure:

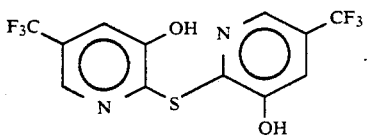

Further elution with 4 percent acetone in hexane gives a second component. Recrystallization gives 1.1 grams (4.4 percent yield) of a light yellow material. The material is analyzed to give a chemical formula of $C_{10}H_2F_3N_3S_3$, but the structure is not characterized. Further elution with 10 percent acetone in hexane and earlier mixed cuts are combined and separated by dry-column. A third component is obtained. Recrystallization from dichloromethane/hexane gives 1.2 grams (5.3 percent yield) of a yellow material which has a melting point of 61° to 63° C. This material is analyzed and found to be 7-(trifluoromethyl)dithiino[2,3-b]pyridine-2,3-dicarbonitrile.

Antimicrobial Activity

The compounds of this invention are useful as antimicrobial additives to such industrial products as styrene-butadiene latexes used for paper coatings, paints, inks, adhesives, soaps, cutting oils, textiles, and paper and pigment slurries. The compounds are also useful as antimicrobial additives in such personal care products as hand creams, lotions, shampoos, and hand soaps. A further advantage of this invention is its cost-effectiveness for applications which need to have an antimicrobial continuously replenished, such as in cooling towers and pulp and paper mills.

As appreciated in the art, the two compounds disclosed herein are not necessarily active at the same concentrations or against the same microbial species. That is, there is some compound-to-compound variation in antimicrobial potency and spectrum of antimicrobial activity.

The present invention is also directed to a method for inhibiting microorganisms which comprises contacting said microorganisms or habitat thereof with an effective amount of the compound of this invention.

The antimicrobial compounds of this invention may be added directly to aqueous formulations susceptible to microbial growth, either undiluted or dissolved in inert diluents such as organic solvents such as glycols, alcohols, or acetone. They may also be added alone or in combination with other preservatives.

As used herein, the term "microorganism" is meant to refer to bacteria, fungi, viruses, algae, subviral agents and protozoa.

As used herein, the term "antimicrobially effective amount" refers to that amount of one or a mixture of both the compounds, or of a composition comprising such compound or compounds, of this invention needed to exhibit inhibition of selected microorganisms. Typically, this amount varies from providing about 1 part per million (ppm) to about 5,000 ppm by weight of the compound to a microbial habitat being contacted with the compound. Such amounts typically vary depending upon the particular compound tested and microorganism treated. Also, the exact concentration of the compounds to be added in the treatment of industrial and consumer formulations may vary within a product type depending upon the components of the formulation. A preferred effective amount of the compound is from about 1 ppm to about 500 ppm, more preferably from about 1 ppm to about 50 ppm by weight, of a microbial habitat.

The term "microbial habitat" refers to a place or type of site where a microorganism naturally or normally lives or grows. Typically, such a microbial habitat will be an area that comprises a moisture, nutrient, and/or an oxygen source such as, for example, a cooling water tower or an air washing system.

The terms "inhibition", "inhibit" or "inhibiting" refer to the suppression, stasis, kill, or any other interference with the normal life processes of microorganisms that is adverse to such microorganisms, so as to destroy or irreversibly inactivate existing microorganisms and/or prevent or control their future growth and reproduction.

The antimicrobial activity of the compounds of the present invention is demonstrated by the following techniques.

TABLE I

| Identification of Compounds used in Antimicrobial Activity Tests | |
|---|---|
| Compound No. | Chemical Identity |
| A | 6-(Trifluoromethyl)dithiolo[4,5-b]pyridine-2-ylidenyl propanenitrile |
| B | 7-(Trifluoromethyl)dithiino[2,3-b]pyridine-2,3-dicarbonitrile |

The minimum inhibitory concentration (MIC) for the compounds listed in Table I is determined for 9 bacteria, using nutrient agar, and 7 yeast and fungi, using malt yeast agar. A one percent solution of the test compound is prepared in a mixture of acetone and water. Nutrient agar is prepared at pH 6.8, representing a neutral medium, and at pH 8.2, representing an alkaline medium. The nutrient agars are prepared by adding 23 g of nutrient agar to one-liter of deionized water. In addition, the alkaline medium is prepared by adjusting a 0.04M solution of N-[tris-(hydroxymethyl)methyl]glycine buffered deionized water with concentrated sodium hydroxide to a pH of 8.5. Malt yeast agar is prepared by adding 3 g yeast extract and 45 g malt agar per liter of deionized water. The specific agar is dispensed in 30 ml aliquots into 25×200 mm test tubes, capped and autoclaved for 15 minutes at 115° C. The test tubes containing the agar are cooled in a water bath until the temperature of the agar is 48° C. Then, an appropriate amount of the one percent solution of the test compound is added (except in the controls where no compound is added) to the respective test tubes so that the final concentrations are 500, 250, 100, 50, 25, 10, 5, 2.5, 1.0 and zero parts per million of the test compound in the agar, thus having a known concentration of test compound dispersed therein. The contents of the test tubes are then transferred to respective petri plates. After drying for 24 hours, the petri plates containing nutrient agar are inoculated with bacteria and those containing malt yeast agar are inoculated with yeast and fungi.

The inoculation with bacteria is accomplished by using the following procedure. Twenty-four hour cultures of each of the bacteria are prepared by incubating the respective bacteria in tubes containing nutrient broth for 24 hours at 30° C. in a shaker. Dilutions of each of the 24 hour cultures are made so that nine separate suspensions (one for each of the nine test bacteria) are made, each containing $10^8$ colony forming units (CFU) per ml of suspension of a particular bacteria. Aliquots of 0.3 ml of each of the bacterial suspensions are used to fill the individual wells of Steer's Replicator. For each microbial suspension, 0.3 ml was used to fill three wells (i.e., three wells of 0.3 ml each) so that for the nine different bacteria, 27 wells are filled. The Steer's Replicator is then used to inoculate both the neutral and alkaline pH nutrient agar petri plates.

The inoculated petri plates are incubated at 30° C. for 48 hours and then read to determine if the test compound which is incorporated into the agar prevented growth of the respective bacteria.

The inoculation with the yeast and fungi is accomplished as follows. Cultures of yeast and fungi are incubated for seven days on malt yeast agar at 30° C. These cultures are used to prepare suspensions by the following procedure. A suspension of each organism is prepared by adding 10 ml of sterile saline and 10 microliters of octylphenoxy polyethoxy ethanol to the agar slant of yeast or fungi. The sterile saline/octylphenoxy polyethoxy ethanol solution is then agitated with a sterile swab to suspend the microorganism grown on the slant. Each resulting suspension is diluted into sterile saline (1 part suspension: 9 parts sterile saline). Aliquots of these dilutions are placed in individual wells of Steer's Replicator and petri plates inoculated as previously described. The petri plates are incubated at 30° C. and read after 48 hours for yeast and 72 hours for fungi.

Table II lists the bacteria, yeast and fungi used in the MIC test described above along with their respective American Type Culture Collection (ATCC) identification numbers.

TABLE II

| Organisms used in the Minimum Inhibitory Concentration Test | |
|---|---|
| Organism | ATCC No. |
| Bacteria | |
| Bacillus subtilis (Bs) | 8473 |
| Enterobacter aerogenes (Ea) | 13048 |
| Escherichia coli (Ec) | 11229 |
| Klebsiella pneumoniae (Kp) | 8308 |
| Proteus vulgaris (Pv) | 881 |
| Pseudomonas aeruginosa (Pa) | 10145 |
| Pseudomonas aeruginosa (PRD-10) | 15442 |
| Salmonella choleraesuis (Sc) | 10708 |
| Staphylococcus aureus (Sa) | 6538 |
| Yeast/Fungi | |
| Aspergillus niger (An) | 16404 |
| Canida albicans (Ca) | 10231 |
| Penicillium chrysogenum (Pc) | 9480 |
| Saccharomyces cerevisiae (Sc) | 4105 |
| Trichoderma viride (Tv) | 8678 |
| Aureobasidium pullulan (Ap) | 16622 |
| Fusarium oxysporum (Fo) | 48112 |

In Tables III and IV, the MIC values of the compounds described in Table I as compared to the MIC of a standard commercial preservative (DOWICIL TM 75, a trademark of The Dow Chemical Company, with 1-(3-chloroallyl)-3,5,7-triaza-1-azoniaadamantane chloride as the active agent) are set forth for the nine bacteria organisms and six yeast/fungi organisms which are listed in Table II.

TABLE III

| Minimum Inhibitory Concentrations for Test Compounds in Bacteria Species (in ppm) | | | | | | | | | |
|---|---|---|---|---|---|---|---|---|---|
| | ORGANISMS | | | | | | | | |
| Compound | Bs | Ea | Ec | Kp | Pv | PRD | Pa | Sc | Sa |
| DOWICIL TM 75 | | | | | | | | | |
| pH 6.8 | 50 | 100 | 100 | 50 | 50 | 100 | 100 | 50 | 100 |
| pH 8.2 | 250 | 250 | 250 | 250 | 250 | 500 | >500 | 100 | 250 |
| (A) pH 6.8 | >500 | >500 | >500 | >500 | >500 | >500 | >500 | >500 | >500 |
| pH 8.2 | >500 | >500 | >500 | >500 | >500 | >500 | >500 | >500 | >500 |
| (B) pH 6.8 | 500 | 500 | 50 | 500 | 50 | 500 | 500 | 100 | 50 |
| pH 8.2 | >500 | >500 | >500 | >500 | >500 | >500 | >500 | >500 | 250 |

TABLE IV

| Minimum Inhibitory Concentrations for Test Compounds in Yeast/Fungi Species (in ppm) | | | | | | | |
|---|---|---|---|---|---|---|---|
| | ORGANISMS | | | | | | |
| COMPOUND | An | Ca | Pc | Sc | Tv | Ap | Fo |
| DOWICIL TM 75 | >500 | >500 | >500 | 500 | >500 | >500 | >500 |
| A | >500 | >500 | >500 | >500 | >500 | >500 | >500 |
| B | <10 | 100 | <10 | 25 | <10 | <10 | <10 |

What is claimed is:

1. A compound corresponding to the formula:

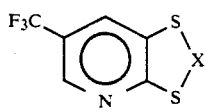

wherein X represents:

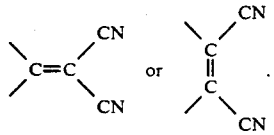

2. The compound of claim 1 wherein X represents:

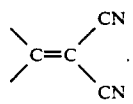

3. The compound of claim 1 wherein X represents:

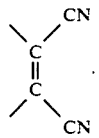

4. The antimicrobial composition comprising a an inert diluent and an antimicrobially effective amount of a compound corresponding to the formula:

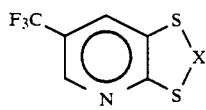

wherein X represents:

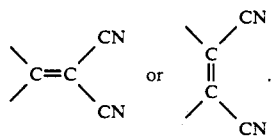

5. The composition of claim 4 wherein X represents:

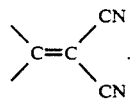

6. The composition of claim 4 wherein X represents:

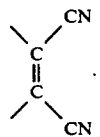

7. The composition of claim 4 wherein the compound is present in the composition in an amount to provide from about 1 part per million to about 5,000 parts per million by weight of the compound to a microbial habitat that is contacted with the composition.

8. A method for inhibiting microorganisms in a microbial habitat comprising contacting said microbial habitat with an antimicrobially effective amount of a compound corresponding to the formula:

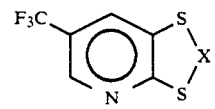

wherein X represents:

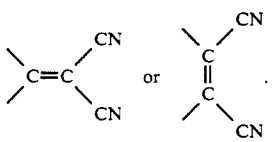

9. The method of claim 8 wherein X represents:

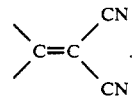

10. The method of claim 8 wherein X represents:

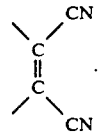

11. The method of claim 8 wherein the compound is present in an amount to provide from about 1 part per million to about 5,000 parts per million by weight of the compound to the microbial habitat.

* * * * *